(12) United States Patent
Jordan et al.

(10) Patent No.: US 6,482,002 B2
(45) Date of Patent: Nov. 19, 2002

(54) ORTHODONTIC APPLIANCE PROVIDING ENHANCED ADHESIVE CURE

(75) Inventors: Russell A. Jordan, Rancho Cucamonga, CA (US); Oscar M. Binder, Anaheim Hills, CA (US); Evangelos G. Georgakis, Alta Loma, CA (US); Oliver L. Puttler, La Crescenta, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/799,241

(22) Filed: Mar. 5, 2001

(65) Prior Publication Data

US 2002/0136999 A1 Sep. 26, 2002

(51) Int. Cl.⁷ .................................. A61C 3/00
(52) U.S. Cl. ........................... 433/9; 433/29
(58) Field of Search .................. 433/29, 8, 9

(56) References Cited

U.S. PATENT DOCUMENTS

| | | |
|---|---|---|
| 2,713,720 A | 7/1955 | Johnson |
| 3,932,940 A | 1/1976 | Andren |
| 3,949,477 A | 4/1976 | Cohen et al. |
| 4,063,360 A | 12/1977 | Waller |
| 4,094,068 A | 6/1978 | Schinhammer |
| 4,216,583 A | 8/1980 | Reynolds |
| 4,219,617 A | 8/1980 | Wallshein |
| 4,256,455 A | 3/1981 | Forster |
| D290,040 S | 5/1987 | Kelly |
| 4,749,352 A | 6/1988 | Nicholson |
| 4,871,786 A | 10/1989 | Aasen et al. |
| 4,952,142 A | 8/1990 | Nicholson |
| 4,954,080 A | 9/1990 | Kelly et al. |
| 4,978,007 A | 12/1990 | Jacobs et al. |
| 5,015,180 A | 5/1991 | Randklev |
| 5,049,068 A | 9/1991 | Sterrett et al. |
| 5,098,288 A | 3/1992 | Kesling |
| 5,110,290 A | 5/1992 | Wong |
| 5,263,859 A | 11/1993 | Kesling |
| 5,304,061 A | 4/1994 | Nelson |
| 5,316,473 A | 5/1994 | Hare |
| 5,332,429 A | 7/1994 | Mitra et al. |
| 5,366,372 A | 11/1994 | Hansen et al. |
| 5,395,237 A | 3/1995 | Pospisil et al. |
| 5,435,720 A | 7/1995 | Riebschleger |
| 5,575,645 A | 11/1996 | Jacobs et al. |
| 5,607,299 A | 3/1997 | Nicholson |
| 5,636,736 A | 6/1997 | Jacobs et al. |
| 5,711,665 A | 1/1998 | Adam et al. |
| 5,813,854 A | 9/1998 | Nikodem |

FOREIGN PATENT DOCUMENTS

| | | |
|---|---|---|
| CA | 2139078 | 6/1995 |
| EP | 385792 | 9/1990 |

OTHER PUBLICATIONS

PCT Patent Application US00/28456.

Primary Examiner—Ralph A. Lewis
(74) Attorney, Agent, or Firm—James D. Christoff

(57) ABSTRACT

An orthodontic appliance includes a base with an outer surface, as well as at least one passageway extending through the base. An element is received in each passageway and is made of a material that transmits actinic radiation. The element serves as a window to facilitate the curing of light-curable orthodontic adhesive beneath the appliance base, while simultaneously preventing movement of the adhesive through the passageway. Optionally, one or more optical fibers are provided to facilitate curing of the adhesive.

40 Claims, 6 Drawing Sheets

ORTHODONTIC APPLIANCE PROVIDING ENHANCED ADHESIVE CURE

BACKGROUND OF THE INVENTION

1. Field of the Invention

This invention broadly relates to appliances that are used during the course of orthodontic treatment. More particularly, the invention relates to orthodontic appliances such as brackets that are directly bonded to the surfaces of teeth, methods for bonding orthodontic appliances to teeth and methods for making orthodontic appliances.

2. Description of the Related Art

Orthodontic treatment involves the movement of malpositioned teeth to orthodontically correct locations. Orthodontic treatment is often undertaken to improve the patient's facial appearance. In addition, orthodontic treatment when completed can provide improved occlusion and help avoid undue wear on the teeth enamel that might otherwise create additional problems in the future.

One type of common orthodontic treatment includes the use of a set of tiny, slotted appliances known as brackets. Each of the brackets is mounted on an outer surface of the patient's tooth, and an archwire is placed in the slot of each bracket. The archwire forms a track to guide movement of the brackets such that the associated teeth are brought into positions of correct alignment. Ends of the archwire are often received in small molar appliances, also called buccal tubes, that are mounted on molar teeth of each dental arch.

Many commercially available orthodontic appliances are adapted to be directly bonded to the outer surface of the patient's teeth by an orthodontic bonding adhesive. Some types of orthodontic adhesives are initially supplied as two separate components, such as CONCISE brand adhesive from 3M Unitek. As the components are mixed together, the components react with each other to form an adhesive that ultimately hardens and provides sufficient strength to bond the appliance to the tooth.

Two-component orthodontic adhesives have a certain "working time". During the working time, the practitioner transfers the mixed adhesive to the base of the appliance, places the appliance on the tooth and shifts the appliance as may be needed to a desired position on the tooth, all before the adhesive begins to harden. However, if the working time is too short or if the practitioner is interrupted during the procedure, the practitioner may not have sufficient time to precisely place the appliance in its intended position on the tooth surface. On the other hand, if the working time is too long, there is a risk that the appliance will shift from its intended position before the adhesive hardens. Unintentional appliance movement may occur, for example, if the appliance is bumped or jarred, or if the adhesive has a viscosity that enables the appliance to drift along the surface of the tooth. Unfortunately, appliances that are mispositioned once bonded to the teeth represent a significant nuisance to the practitioner as well as to the patient, especially in instances when the appliance must be removed from the tooth and rebonded at the correct location.

For the reasons set out above, many orthodontic practitioners prefer to use a photopolymerizable adhesive that begins to harden once a source of light is directed toward the adhesive. Photopolymerizable adhesives, also known as light-curable adhesives, are used by many orthodontic practitioners because the length of the working time can be chosen as needed. For example, an appliance with a light-curable adhesive can be carefully placed on the patient's tooth and shifted as desired until such time as the practitioner is satisfied with the position of the appliance. At that time, a source of light is directed toward the adhesive in order to harden the adhesive and quickly fix the appliance to the tooth.

Over the years, many attempts have been made to increase the strength of the bond between orthodontic appliances and the associated teeth. Some brackets, for example, have an outer base surface that is roughened, scribed or dimpled, while other brackets have a base surface that includes one or more layers of irregularly shaped fragments or spherical particles. Such base surfaces present an increased surface area that is available for contact with the adhesive, in order to improve the strength of the bond between the appliance and the tooth.

Additionally, certain orthodontic appliances have bases that present undercut regions to receive the adhesive. Once the adhesive has hardened, the adhesive in the undercut regions forms a mechanical interlock with the appliance. As an example, the bases of some appliances have a fine mesh metal "screen" or pad that becomes embedded in the adhesive and provides a mechanical interlock with the adhesive once the adhesive has hardened. Other appliances, such as that shown in U.S. Design Pat. No. 290,040, have a series of undercut grooves that provide a mechanical interlock with the hardened adhesive. U.S. Pat. Nos. 4,094,068 and 5,435,720 describe appliances having bases with peripheral holes or notches that enable the adhesive to flow through and produce an enlarged head that serves to improve retention of the appliance on the tooth. Orthodontic appliances may also have irregularly-shaped fragments or spherical particles that present undercut regions.

Orthodontic appliances are available in a variety of materials, including metallic materials (such as stainless steel and titanium), plastics (such as filled and/or reinforced polycarbonate) and ceramics (such as monocrystalline and polycrystalline alumina). Some orthodontic practitioners and patients prefer appliances that are made of transparent or translucent materials such as certain plastics and ceramics, because those appliances can blend in with the color of the patient's teeth and as a result are less noticeable in the oral cavity. Some orthodontic appliances, such as those described in applicants U.S. Pat. No. 4,954,080, are made of a polycrystalline alumina material that has sufficient translucency to enable the color of the tooth to be visible through the appliance in order to provide an enhanced aesthetic appearance.

When a photopolymerizable orthodontic adhesive is used in combination with an appliance that is made of a translucent or transparent material, light passing through the appliance can normally reach the underlying adhesive. As a result, the adhesive is usually hardened to a substantial extent under most, if not all, portions of the appliance base. The extent of hardening of the adhesive helps ensure that the appliance does not spontaneously debond from the patient's tooth during the course of orthodontic treatment.

Many practitioners, however, prefer to use orthodontic appliances that are made of materials other than light-transmissive plastic and ceramic materials. For example, a substantial number of orthodontists prefer to use appliances made of stainless steel. Although stainless steel appliances are often not considered aesthetic, many practitioners choose stainless steel appliances because they are relatively inexpensive and yet provide satisfactory control over movement of the associated teeth.

However, stainless steel is an opaque material that blocks passage of light to underlying areas of the appliance base. As a consequence, portions of photopolymerizable adhesive beneath the base may not harden, especially in areas near the center of the base. Often, the practitioner may direct light toward the adhesive along two or more edges of the base of metal appliances or attempt to direct light through the patient's tooth enamel. However, such a practice may not harden all of the adhesive beneath the base to a degree necessary to preclude unintentional debonding of the appliance when the appliance is subjected to a relatively large force.

U.S. Pat. No. 5,711,665, assigned to the assignee of the present invention, describes a method and apparatus for bonding orthodontic appliances to teeth. The appliance includes a base with an opening, and a body with a passage aligned with the opening. The passage in the appliance permits light to reach adhesive beneath a central portion of the appliance base that would otherwise remain substantially uncured. As a result, bond strength between the appliance and the tooth is increased and the likelihood of unintentional, spontaneous debonding of the appliance during the course of treatment is significantly reduced.

While the inventions described in U.S. Pat. No. 5,711,665 constitute a significant advance in the art, there is a continuing need to improve the construction of orthodontic appliances and methods of orthodontic treatment. Preferably, such improvements can be adopted with relatively little additional expense, and yet significantly enhance the state of the art such that the practitioner and the patient can both benefit from the improvements.

SUMMARY OF THE INVENTION

The present invention is directed to an orthodontic appliance that has a base and at least one passageway extending through the base. An element is received in the passageway and is made of a material that transmits actinic radiation. The element functions as a "window" to enable light to reach underlying regions of the appliance base so that hardening of the adhesive is facilitated. The window also hinders movement of the adhesive through the passageway as the appliance is placed on the tooth surface, such that the necessity of clean-up of adhesive near the front side of the passageway is avoided.

Optionally, the element is made of a material that slowly releases fluoride in order to inhibit the formation of caries in the vicinity of the appliance. As another option, the element is made of a material that transmits actinic radiation, but also is tinted to provide a certain color when viewed by the practitioner. The color may be selected from a set of colors that are part of a color-coding system to identify certain types of appliances, or to identify the type or location of the tooth on which the appliance is to be mounted.

As an additional option, the element may include one or more optical fibers to facilitate transmission of light to the adhesive. As an example, a number of optical fibers may be embedded within a portion of the element that is received in the passageway, and the fibers may extend radially outwardly toward a periphery of the appliance base. When actinic radiation is directed toward the element, a portion of the light passes through the fibers and to regions of the adhesive that are remote from the passageway.

In more detail, the present invention in one aspect concerns an orthodontic appliance for attachment to a tooth. The appliance includes a base having an outer surface and a body extending from the base in a direction away from the outer surface. The orthodontic appliance also includes a slot next to the body for receiving an archwire, and a passageway extending through the base. The orthodontic appliance additionally includes an element that extends in the passageway. The element is made of a material that transmits actinic radiation.

Another aspect of the invention is directed toward a method of bonding an orthodontic appliance to a tooth. The method includes the act of providing an orthodontic appliance having a passageway that extends toward a base of the appliance and an element extending in the passageway. The method also includes the acts of placing a quantity of photocurable adhesive on the base of the appliance, and placing the appliance on the tooth. The method further includes the act of directing actinic radiation through the passageway and the element in order to facilitate curing of the adhesive.

An additional aspect of the invention is directed toward an orthodontic assembly. The assembly includes an orthodontic appliance having a base with an outer surface. The assembly also includes an orthodontic adhesive that extends along at least a portion of the outer surface. The assembly further includes at least one optical fiber that is received in the adhesive and extends along the base.

The present invention is also directed toward a method of bonding an orthodontic appliance to a tooth. This method includes the acts of providing an orthodontic appliance having a base with an outer surface, and placing a quantity of light-curable adhesive on the outer surface. The method also includes the acts of placing at least one optical fiber in the adhesive, and positioning the appliance on the tooth. The method further includes the act of directing a source of actinic radiation toward the at least one optical fiber in order to enhance distribution of the actinic radiation in the adhesive.

The present invention is further directed toward a method of making an orthodontic appliance. This method includes the acts of providing a ring having a channel extending along an inner peripheral surface, and making a series of passageways through the ring in generally radial directions, wherein at least some of the passageways extend into the channel. The method also includes the acts of directing a polymeric material into the channel and into at least some of the passageways, and hardening the polymeric material. The method further includes the act of shaping a number of appliance from each ring, wherein each appliance includes a portion of the channel, at least one passageway and a portion of the hardened polymeric material.

Other aspects of the invention are described in more detail below and are illustrated in the accompanying drawings.

DETAILED DESCRIPTION OF THE PREFERRED EMBODIMENTS

Figure 1:
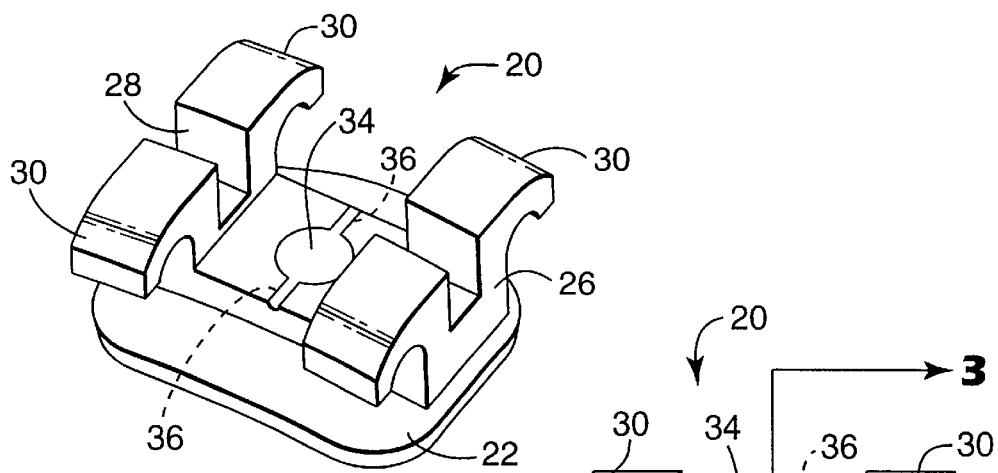
FIG. 1 is a perspective view of an orthodontic appliance constructed in accordance with one embodiment of the invention.
Figure 2:
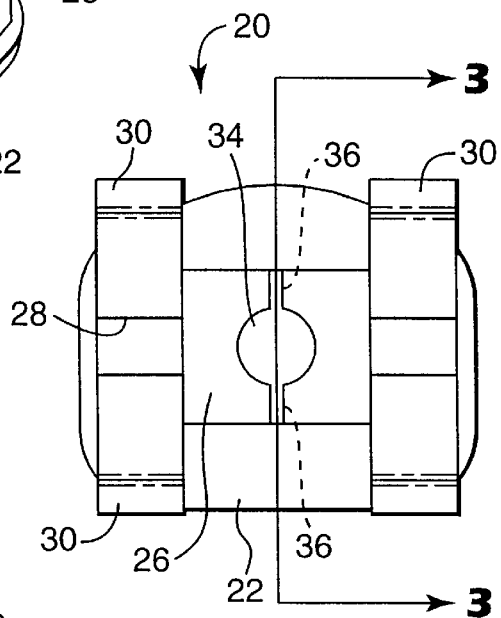
FIG. 2 is a front elevational view of the appliance shown in FIG. 1.
Figure 3:
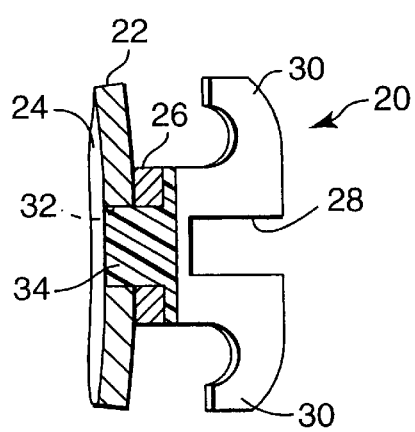
FIG. 3 is a side cross-sectional view of the appliance shown in FIGS. 1 and 2 and taken along lines 3—3 of FIG. 2.

An orthodontic appliance according to one embodiment of the invention is illustrated in FIGS. 1–3 and is broadly designated by the numeral 20. The appliance 20 in this instance is a bracket that includes a base 22 with an outer surface 24 (see FIG. 3). Preferably, the outer surface 24 has a compound contour that matches the convex shape of the tooth intended to receive the appliance 20. However, the outer surface 24 may also be flat or have any other shape as desired.

A body 26 of the appliance 20 extends from the base 22 in a direction away from the outer surface 24. As an example, if the appliance 20 is intended to be bonded on the facial or buccolabial surfaces of the patient's teeth, the body 26 extends outwardly from the base 22 in a buccolabial direction. However, the appliance 20 may also be a lingual appliance adapted for bonding to the lingual, or tongue-facing surfaces of a tooth. The base 22 may be integral with the body 26, or alternatively may be manufactured separately and fixed to the body 26 in a subsequent operation (for example, by a spot-welding or brazing process).

An elongated archwire slot 28 extends next to the body 26 for receiving an archwire (not shown). In the illustrated embodiment, the body 26 includes four tiewings 30, and the archwire slot 28 extends through a space between adjacent pairs of tiewings 30. However, other embodiments are also possible. For example, the body 26 may have only one pair of tiewings, and the archwire slot may extend through a space between those tiewings. As another example, the body 26 may lack an open slot and instead have a closed slot in the form of a tubular channel for receiving an archwire, as is found in buccal tube appliances.

As shown for example in FIG. 3, a passageway 32 extends through the base 22. In this embodiment, the passageway 32 is located in the center of the base 22 and also extends through a central portion of the body 26. However, the passageway 32 may be placed in other locations, and need not extend through the body 26 if desired.

An element 34 extends through the passageway 32, and preferably is fixed in place in the passageway 32. The element 34 is made of a material that transmits actinic radiation. The element 34 is capable of transmitting actinic radiation having a wavelength sufficient to initiate polymerization of a light-curable orthodontic adhesive as will be described in more detail below.

Optionally, the tooth-facing side of the element 34 is flush or approximately flush with the outer surface 24 as shown in FIG. 3. Preferably, the opposite side (i.e., the "front" side) of the element 34 is flush or approximately flush with the surfaces surrounding the entrance to the passageway 32 (in this embodiment, the surfaces surrounding the passageway entrance are located on the central, buccolabial side of the central portion of the body 26). In this manner, the presence of a cavity or recess that might otherwise tend to retain food or other debris is avoided.

As an additional option, the front side of the element 34 has a configuration or structure that facilitates receiving actinic radiation. For example, the front side may have a domed or convex shape that serves to focus or shape the light beam and/or facilitate the reception of a light beam that is somewhat out of alignment with the central axis of the passageway 32. As another option, the front side of the element 34 may have structure that optically and/or mechanically couples to a light source or otherwise enhances the transfer of light from the source of the element 34.

The body 26 also includes a pair of elongated grooves 36 that extend from the passageway 32. The grooves 36 are optional but are preferably provided in order to facilitate alignment of the appliance 20 to the long axis of the patient's tooth. Preferably, the grooves 36 are parallel with the direction of extension of the tiewings 30 away from the longitudinal axis of the archwire slot 28.

Optionally, the element 34 presents a color that is visible to the practitioner during initial handling and placement of the appliance 20, but does not substantially hinder the passage of actinic radiation through the element 34. Preferably, the selected color is one of a set of colors that serve to identify the tooth for which the appliance 20 is intended. For example, a red color may indicate that the appliance 20 is intended for an upper bicuspid tooth while a green color may indicate that the appliance 20 is intended for an upper cuspid tooth. In this manner, the appliances are color-coded to facilitate identification and to help ensure that the appliances are mounted on proper, respective teeth.

Preferably, but not necessarily, the element 34 includes a pair of opposed arm portions that are received in the grooves 36. The arm portions tend to improve the visibility of the grooves 36, particularly if the element 34 (including the arm portions) are colored. As a result, identification of the appliance 20 by use of the color-coding described above is enhanced and alignment of the appliance 20 with the long axis of the tooth is facilitated.

The element 34 may be manufactured separately and fixed in place in the passageway 32 by an adhesive, by friction fit or any other suitable means. Alternatively, the element 34 may be made by immersing the passageway 32 in a liquid polymer that ultimately hardens. Preferably, the liquid polymer not only fills the passageway 32 during immersion, but also fills the grooves 36.

Figure 4:
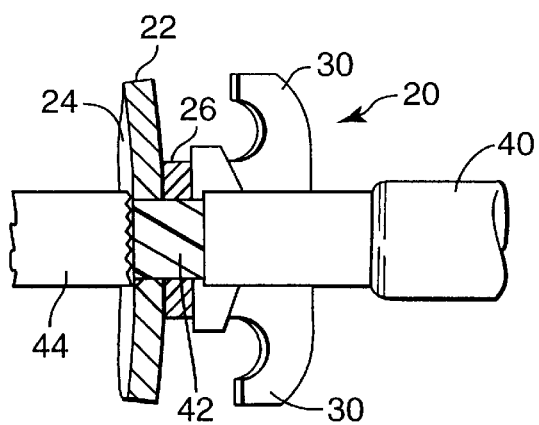
FIG. 4 is a view somewhat similar to FIG. 3, except that FIG. 4 also depicts in schematic form an injector for making an element of the appliance according to one preferred method.

An alternative method for making the element 34 is illustrated schematically in FIG. 4. As shown, a nozzle 40 having an outer end that matches the shape of the passageway 32 in the grooves 36 is placed over the body 26 in sealed relation. A quantity of curable polymeric material 42 is directed through the nozzle 40 and into the passageway 32 as well as into the grooves 36.

As depicted in FIG. 4, a stop 44 is placed against the outer surface 24 in an area surrounding the passageway 32. The stop 44 serves to prevent the polymeric material 42 from escaping the passageway 32. The stop 44 is held in place until the polymeric material 42 has hardened. Optionally, the stop 44 has a roughened surface that faces the passageway 32, so that the polymeric material 42 also has a roughened surface once it has hardened. The roughened surface of the resulting element 34 serves to enhance the bond of the polymeric element 34 to the orthodontic adhesive that is used to bond the appliance 20 to the patient's tooth.

An example of a suitable polymeric material for making the element 34 is TRANSBOND™ orthodontic adhesive primer from 3M Unitek. Preferably, a quantity of fluoride is added to the polymeric material prior to placement of the material in the passageway 32. The fluoride preferably releases relatively slowly from the polymeric material during the course of orthodontic treatment, in order to provide a source of fluoride to adjacent enamel surfaces of the patient's teeth and reduce the likelihood of caries formation. The formation of caries is a particular problem with orthodontic patients, because the appliances, archwires and other orthodontic devices in the oral cavity may tend to retain or entrap food.

The source of fluoride may be an inorganic fluoride source, an organic fluoride source or both. Inorganic fluoride salts include simple and complex metal fluoride salts as well as fluoride glasses, e.g., fluoroaluminosilicate glass. Particularly preferred inorganic sources of fluoride include silanol treated fluoroaluminosilicate glass fillers such as described in U.S. Pat. No. 5,332,429, the disclosure of which is expressly incorporated by reference herein. Particularly preferred organic sources of fluoride include tetrafluoroborate salts such as described in U.S. Pat. No. 4,871,786, the disclosure of which is also expressly incorporated by reference herein.

An example of a preferred polymeric material containing a source of fluoride is set out below, in parts by weight:

TABLE I

| INGREDIENT | PARTS |
| --- | --- |
| hydroxy ethyl methacrylate ("HEMA") | 62.9 |
| virebond co-polymer ("VBC") | 20.96 |
| glyceryl dimethacrylate ("GDMA") | 10.48 |
| dimethylaminoethyl methacrylate methyl tetrafluoroborate ("DMAEMA") | 2.52 |
| camphorquinone ("CPQ") | 0.52 |

TABLE I-continued

| INGREDIENT | PARTS |
| --- | --- |
| ethyl-4-dimethylaminobenzoate ("EDMAB") | 0.52 |
| diphenyliodonium hexafluorophosphate ("DPIHFP") | 1.05 |
| distilled water | 2.52 |

The use of DMAEMA, as exemplified in Table I, is an advantage because DMAEMA is a monomer and as a result cures with the other monomer components to create a highly crosslinked matrix. Since DMAEMA dissolves in the other monomers, the resulting cured polymeric material is highly transparent and provides relatively little scattering of light.

As yet another option, a composition containing fluoride could be placed on the appliance 20 in an operation distinct from making the element 34. For example, the element 34 could be made by immersing the passageway 32 (and preferably the grooves 36) in a liquid polymer as described above, and subsequently a quantity of fluoride composition could be placed on a surface of the element 34 or another surface of the appliance 20. The fluoride composition could be added by immersing the appliance or by spraying a liquid composition containing fluoride onto all or a portion of the appliance 20, with or without the use of a robotic arm. If desired, the element 34 could be slightly smaller than illustrated in the drawings and the fluoride composition placed on the element 34 in the passageway 32 in sufficient quantity to render the outer surface of the composition containing the fluoride in flush relation with adjacent surfaces of the appliance 20. In this instance, the composition containing the fluoride should be capable of transmitting actinic radiation so that it does not impair the function of the element 34.

Other materials for making the element 34 may also be used. An example of a suitable alternative material is an orthodontic glass ionomer cement such as Fuji "Ortho LC" brand cement from GC Dental Company. Preferably, the cement includes a quantity of fluoride. Another alternative material is polycarbonate, such as a "CD grade" polycarbonate having good optical characteristics.

The base 22 and the body 26 may be made of any one of a number of materials. For example, the base 22 and the body 26 may be integrally made of a metallic material such as stainless steel Series 300, Series 400 or 17-4 PH. The base 22 and the body 26 may be machined, or may be molded using, for example, a metal injection molding process. As an alternative to stainless steel, the base 22 and the body 26 may be made of other alloys including alloys containing titanium. As an additional option, the base 22 and the body 26 may be made of a precipitation hardening martensitic alloy such as described in applicant's PCT Application No. US00/28456.

As another alternative, the base 22 and the body 26 may be manufactured as two initially separate components that are subsequently fixed to each other. For example, the body 26 could be made of any one of the materials described above, and the base 22 may be made of a material that resembles a fine wire mesh screen. Optionally, a layer of metallic foil extends between the wire screen and the body 26. If the base 22 is made of a wire mesh, the base 22 may be fixed to the body 26 by a brazing process.

When the base 22 and the body 26 are manufactured as two initially separate components, an automated assembly process may be employed to join the components together. For example, a first holding tool could have a pin to enter the portion of the passageway 32 that is in the body 26, and also include a bar member that is received in the archwire slot 28. The pin and the bar member provide orientation of the body 26 relative to the first holding tool. A second holding tool is provided to support the base 22 during assembly. Optionally, a number of identical bases are joined together by runners that were manufactured in a previous process (e.g. mesh bases and runners that were die-cut from a section of mesh and foil stock). The runners provide alignment of each base relative to the second holding tool. Optionally, a pin of the second holding tool could enter the portion of the passageway 32 of each base to aid in precise alignment of the base with the corresponding body. A laser welder is then directed toward the base from the tooth-facing side of the appliance in order to join the two parts together.

To bond the appliance 20 to a tooth, a quantity of orthodontic adhesive is placed on the outer surface 28 and the appliance 20 is then positioned over the selected area of the patient's tooth. Next, the appliance 20 is pressed against the surface of the tooth by finger pressure. Preferably, a sufficient amount of finger pressure is utilized and there is a sufficient amount of adhesive present beneath the outer surface 24 such that a portion of the adhesive is extruded along the entire periphery of the base 22. In this manner, the practitioner can be assured that a sufficient amount of adhesive is present to securely bond the appliance 20 to the tooth. In addition, such practice reduces the likelihood of gaps or voids between the outer surface 24 and the tooth surface.

Next, the practitioner may review the position of the appliance 20 relative to the tooth and shift the appliance 20 as needed in order to place the appliance 20 in the precise, desired position on the tooth. For example, the practitioner may shift the appliance 20 until the archwire slot 28 is exactly aligned with the occlusal plane of the patient and the edges of the tiewings 30 and the grooves 36 are exactly aligned with the longitudinal axis of the tooth. Once the practitioner is satisfied with the position of the appliance 20, a source of light is directed toward the adhesive in order to fix the appliance 20 in place.

If desired, the source of light can be initially directed only through the element 34 in order to harden only the adhesive directly beneath the element 34 and temporarily tack the base 22 to the patient's tooth. The excess adhesive that was previously extruded from the peripheral edge of the appliance base 22 can then be readily removed without dislodging the appliance 20 from its intended position. For example, the practitioner may use a dental explorer or other tool to remove the extruded, uncured adhesive from the tooth adjacent the peripheral edge of the base 22.

Subsequently, remaining portions of the adhesive between the base 22 and the tooth are hardened by directing light toward the peripheral edges of the base 22. If desired, a different curing light assembly may be used for peripheral curing, such as an assembly that emits a greater intensity of light or a wider beam of light.

As can be appreciated, the element 34 functions as a window to permit the passage of actinic radiation to portions of the adhesive beneath the passageway 32. In addition, the element 34 closes and preferably seals the passageway 32 shut so that the collection of food or other debris is not facilitated.

If desired, a curing light assembly having structure that controls movement of the appliance 20 and/or provides orientation of the appliance 20 may be utilized as a source of actinic radiation in bonding the appliance 20 of the present invention. With minor modification, an example of a suitable curing light assembly is illustrated in U.S. Pat. No. 5,711,665 which is incorporated by reference herein. Preferably, the curing light assembly described in U.S. Pat. No. 5,711,665 is modified such that the outer, dome-shaped end portion does not extend as far as shown in that patent so that interference with the element 34 is avoided.

Figure 5:
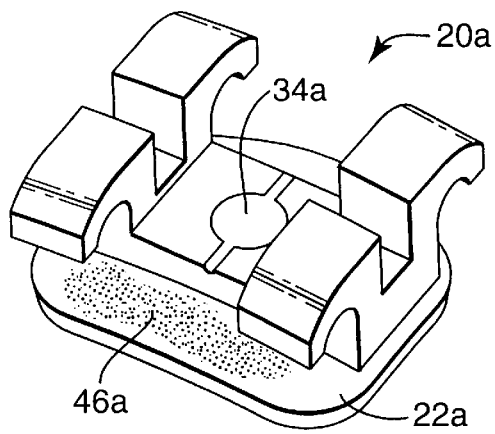
FIG. 5 is a view somewhat similar to FIG. 1, except that FIG. 5 depicts an orthodontic appliance that is constructed in accordance with another embodiment of the invention.

An orthodontic appliance 20a according to another embodiment of the invention is illustrated in FIG. 5. Except for the differences described below, the appliance 20a is identical to the appliance 20. As such, a detailed description of the common aspects need not be repeated.

The appliance 20a includes a layer 46a of material that extends along at least a portion of a base 22a. Preferably, but not necessarily, the layer 46a of material is the same composition as the material of an element 34a (which is identical to the element 34 described above). If the material includes fluoride, the layer 46a advantageously provides an increased area from which fluoride can be released during the course of treatment.

The layer 46a may extend along a tooth-facing outer surface (not shown) of the base 22a, across an opposite surface of the base 22a (as shown), or both. As an option, the element 34a and the layer 46a may be made by immersing the base 22a as well as the passageway in a reservoir containing a quantity of liquid polymeric material. Optionally, the immersion process can be carried out by use of a robotic arm that grips tiewings of the appliance 20a. The liquid polymeric material is then allowed to harden in order to fix the element 34a as well as the layer 46a in place.

Immersing the base 22a as well as at least a portion of the body 26a provides another important advantage, in that small recesses and cavities in the appliance 20a are filled. For example, when the base 22a and the body 26a are initially manufactured as separate components and subsequently joined together, a slight gap might exist between facing surfaces of the base 22a and body 26a. In that instance, the liquid polymeric material tends to fill the gap and provide a seal. As a consequence, the formation of corrosion in the gap is hindered and the likelihood of food accumulation in the gap is reduced.

As an additional option, the base 22a may be made of one or more layers of fine wire mesh, and the foil backing (normally next to the mesh) omitted. The polymeric material, once hardened, provides a backing for the mesh. Also, the polymeric material is preferably made of a composition that securely bonds by forces of adhesion to the orthodontic adhesive that is used to bond the appliance 20a to the patient's tooth. Preferably, the polymeric material is colorless when hardened or presents a color that matches the color of the patient's teeth. If the hardened polymeric material is colorless or matches the color of the patient's teeth, the resulting appearance of the base 22a may render the base 22a more difficult to see in ordinary view. In that instance, the appliance 20a will provide a more aesthetic appearance in the oral cavity.

Figure 6:
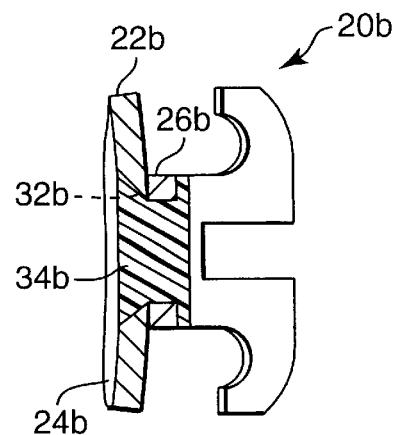
FIG. 6 is a view somewhat similar to FIG. 3, except that FIG. 6 illustrates an orthodontic appliance constructed in accordance with yet another embodiment of the invention.

An orthodontic appliance 20b according to another embodiment of the invention is illustrated in FIG. 6 in side-cross sectional view. Except for the differences noted below, the orthodontic appliance 20b is the same as the appliances 20, 20a.

The appliance 20b has a base 22b as well as a body 26b. A passageway 32b extends through the base 22b and the body 26b. However, at least a portion of the passageway 32b has a chamfered configuration such that the cross sectional area of the passageway 32b increases as a tooth-facing outer surface 24b of the base 22b is approached. Preferably, an element 34b (which is otherwise identical to the element 34) has an outer configuration that matches the internal shape of the passageway 32b including the chamfered portion.

In the illustrated embodiment, the portion of the passageway 32b that passes through the base 22b is chamfered, while the portion of the passageway 32b that passes through the body 26b has a cylindrical configuration. However, other constructions are also possible. For example, the passageway 32b may steadily increase in cross-sectional area along its entire length as the outer surface 24b is approached.

The chamfered portion of the passageway 32b helps to retain element 34b in place in the passageway 32b. For example, when the appliance 20b is pressed against the tooth surface, the adhesive that extends across the outer surface 24b is placed under pressure, which results in a certain amount of pressure being applied to the side of the element 34b that is adjacent the outer surface 24b. The chamfered portion of the passageway 32b, in combination with the resulting chamfered cross-sectional area of the element 34b, ensures that the element 34b does not move in the passageway 32b in a direction away from the outer surface 24b during such a bonding procedure.

Figure 7:
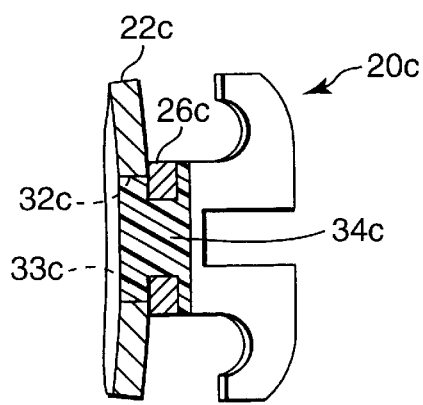
FIG. 7 is a view somewhat similar to FIG. 3, except that FIG. 7 depicts an orthodontic appliance that is constructed in accordance with still another embodiment of the invention.

An orthodontic appliance 20c according to another embodiment of the invention is illustrated in FIG. 7. Except as noted below, the appliance 20c is identical to the appliance 20b described in connection with FIG. 6.

The appliance 20c has a base 22c and a body 26c. A passageway 32c extends through the base 22c and the body 26c. However, the portion of the passageway 32c that extends through the base 22c has a larger cross-sectional area than the cross-sectional area of all portions of the passageway 32c that extends through the body 26c. The step-wise reduction in cross-sectional area presents a shoulder 33c in the passageway 32c.

The appliance 20c also includes an element 34c that is received in the passageway 32c. A portion of the element 34c that is in the passageway 32c preferably has a configuration that matches the configuration of the passageway 32c, including the shoulder 33c. Other aspects and options of the element 34c are similar to the elements 34, 34b described above.

The shoulder 33c helps retain the element 34c in the passageway 32c. As a result, when the appliance 20c is pressed against the tooth surface, the orthodontic adhesive located between the base 22c and tooth surface does not shift the element 34c in the passageway 32c. The shoulder 33c functions in a manner somewhat similar to the chamfer of the passageway 32b described above.

Figure 8:
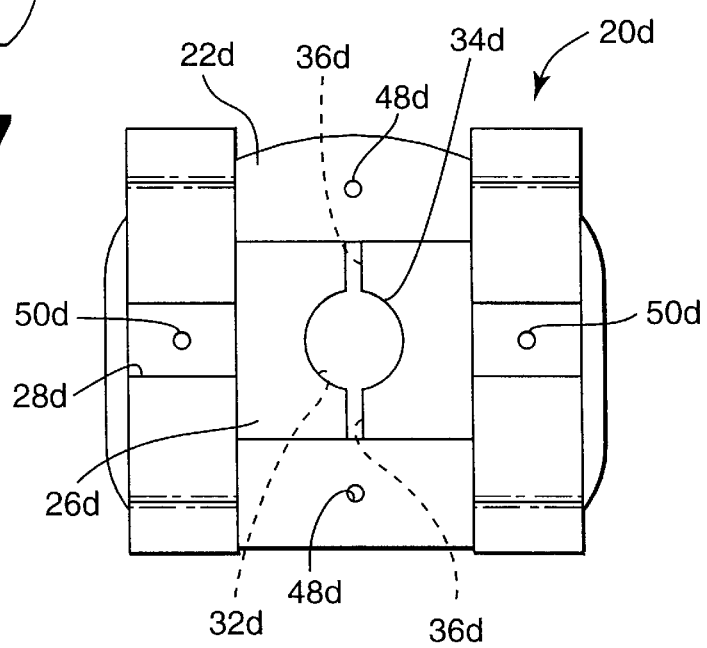
FIG. 8 is a view somewhat similar to FIG. 2, except that FIG. 8 illustrates an orthodontic appliance that is constructed according to an additional embodiment of the invention.

An orthodontic appliance 20d according to another embodiment of the invention is illustrated in FIG. 8. Except as described below, the appliance 20d is identical to the appliance 20 set out above.

The appliance 20d includes a base 22d and a body 26d that is fixed to the base 22d. A passageway 32d extends through a central portion of the body 26d as well as through a central portion of the base 22d. An element 34d is received in the passageway 32d.

The appliance 20d also includes additional passageways 48d, 50d. In the illustrated embodiment, two passageways 48d extend through the base 22d on opposite sides of the passageway 32d and in alignment with grooves 36d. Two passageways 50d extend through the base 22d as well as through the body 26d in a location underlying an archwire slot 28d.

Preferably, each of the passageways 32d, 48d, 50d receives an element that transmits actinic radiation, such as the element 34 described above. Optionally, the passageways 48d, 50d are arranged along reference lines that are useful for aligning the appliance 20d in a certain orientation for facilitating orthodontic treatment. For example, the passageways 48d could be arranged along reference lines that are parallel to the long axis of the patient's tooth while the passageways 50d are arranged along a plane that is parallel to the occlusal plane. However, other arrangement, patterns or locations for the passageways 32d, 48d, 50d are also possible.

Moreover, a greater or smaller number of passageways may be provided than the number shown in FIG. 8. Additionally, the central passageway 32d may be omitted if desired. The passageways 32d, 48d, 50d may also have a cross-sectional area that is larger or smaller than that shown in the drawings for exemplary purposes.

The elements received in the passageways 32d, 48d, 50d may be color-coded if desired as described above in connection with the appliance 20. Since the passageways 48d are relatively small, the elements in the passageways 48d will not be readily visible to a casual observer. The elements in the passageways 50d will be covered from ordinary view by the archwire, as will the majority of the element that is received in the passageway 32d.

Figure 9:
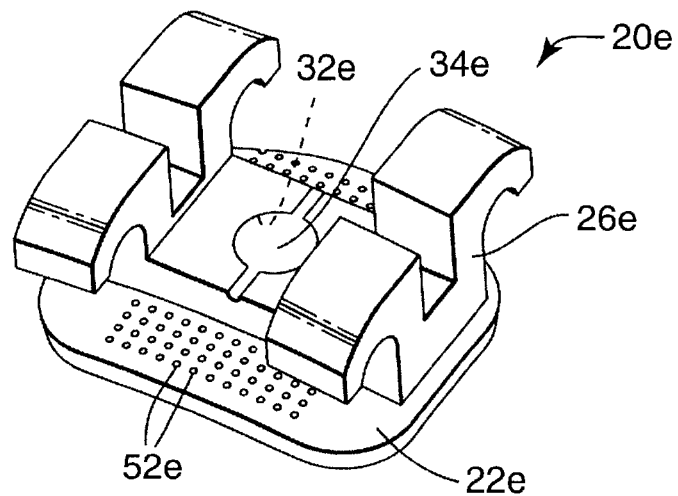
FIG. 9 is a view somewhat similar to FIG. 1, except that FIG. 9 illustrates an appliance that is constructed according to a further embodiment of the invention.

An orthodontic appliance 20e according to yet another embodiment of the invention is illustrated in FIG. 9. Except as described below, the appliance 20e is identical to the appliance 20, and may optionally include the aspects mentioned in connection with the appliances 20a, 20b, 20c, 20d if desired. The appliance 20e has a base 22e and a body 26e that is fixed to the base 22e. The appliance 20e also optionally has a passageway 32e as shown in FIG. 9, and an element 34e is received in the passageway 32e.

The base 22e has an array of any small passageways 52e that extend through the base 22e. The appliance 20e is depicted for exemplary purposes with a rectangular array of many small passageways 52e. However, other arrangements and/or arrays are also possible. Moreover, the passageways 52e may extend in other portions of the base 22e, including side portions or alternatively portions that extend along the entire periphery of the base 22e if desired.

An element is preferably received in each passageway 52e, and is made of a material identical to the elements described above such as the element 34. The large number of passageways 52e helps facilitate hardening of the orthodontic adhesive along a substantial portion of the outer surface of the base 22e. The passageways 52e may be made by a milling or machining operation.

As an additional option, the appliance 20e may be provided with aspects of the appliances 20a, 20b, 20c, 20d and described above. If the appliance 20 is a buccal tube, the passageways are preferably only present in mesial and distal flange portions of the base.

Figure 10:
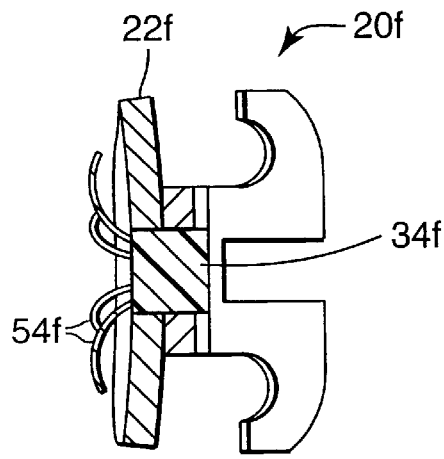
FIG. 10 is a view somewhat similar to FIG. 3, except that FIG. 10 shows an orthodontic appliance with an element that is different than the element shown in FIG. 3 according to still another embodiment of the invention.
Figure 11:
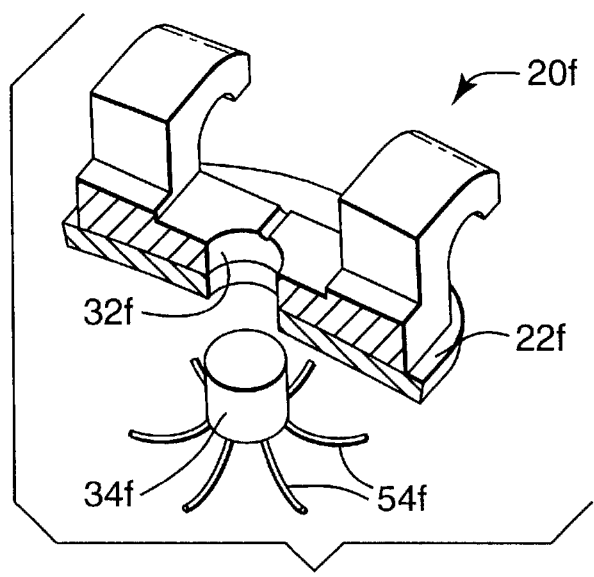
FIG. 11 is an exploded, perspective view depicting a portion of the appliance shown in FIG. 10.

An orthodontic appliance 20f according to another embodiment of the invention is illustrated in FIGS. 10 and 11. Except for the differences noted below, the appliance 20f is identical to the appliance 20 set out above.

The appliance 20f has a passageway 32f that receives an element 34f. The element 34f in this instance includes one or more protrusions. Preferably, the protrusions are optical fibers 54f although other protrusions are also possible. In the illustrated embodiment, six optical fibers 54f are provided and extend outwardly in a generally radial direction from the passageway 32f. However, a greater or smaller number of optical fibers 54f may alternatively be provided, and the optical fibers 54f may be placed in an arrangement having a somewhat different configuration.

Preferably, the optical fibers 54f extend in directions from the passageway 32f toward a periphery of the appliance base 22f. Consequently, when actinic radiation is directed toward the facial side of the element 34f, a portion of the actinic radiation travels along the optical fibers 54f to regions of the orthodontic adhesive that are remote from the passageway 32f. As a result, the optical fibers 54f help ensure that a substantial portion, if not all, of the orthodontic adhesive beneath the base 22f has sufficiently hardened.

Moreover, the optical fibers 54f function as a support substrate or scrim for the adhesive, a particular advantage when the adhesive has a relatively low viscosity. The optical fibers 54f help to retain the adhesive in place and prevent drift of the appliance until such time as the adhesive has hardened. The optical fibers 54f provide body to the adhesive, and yet do not increase the viscosity of the adhesive. As such, the adhesive can readily conform to the exact shape of the tooth enamel when the appliance is pressed against the tooth during bonding.

The element 34f may be made by any suitable technique. In one preferred technique, the optical fibers 54f are initially separate and are placed as a bundle into the passageway 32f. While the optical fibers 54f are held in place in the passageway 32f, a quantity of liquid polymeric material is directed into the passageway 32f and allowed to harden. The resulting element 34f contains embedded fibers 54f that are securely connected to the hardened polymeric material.

As another option, the element 34f is integrally made as a single, unitary component, with tentacles that extend outwardly to form the optical fibers 54f. The element 34f may be made initially separate from the remaining elements of the appliance 20f, or may be molded in place in the passageway 32f if desired. The appliance 20f may also include options described in connection with the appliances 20a–20e mentioned above.

As used herein, "optical fibers" mean any fiber that transmits or facilitates the transmission of actinic radiation. Optical fibers include conventional optical fibers having a cladding or coating, such as "TECS" brand coated silica/silica fibers from 3M Company. Optical fibers also include fibers that are uncoated and unclad, since such fibers may be useful for transmitting actinic radiation to portions of adhesive that may not otherwise receive such radiation. If the optical fibers are clad, the cladding may be interrupted by notches, grooves or other structure to facilitate the escape of actinic radiation along sides of the fiber. The fibers may also be in the form of a woven or nonwoven mesh, optionally along with other types of fibers. If the fibers are in the form of a mesh, the mesh may interlock with the adhesive once the adhesive has hardened in order to increase the bond strength between the appliance and the tooth.

As an additional option, any of the appliances 20–20f may include a layer of light-curable adhesive that is pre-coated onto the appliance before the appliance is packaged for shipment to the practitioner. Examples of adhesive pre-coated orthodontic appliances and suitable adhesives are described for example in U.S. Pat. Nos. 4,978,007, 5,015,180, 5,575,645, and 5,636,736, all of which are expressly incorporated by reference herein.

As a further option, the appliances 20–20f may be initially connected to an optical fiber that leads to a source of actinic radiation. The optical fiber in this instance may lead to a source of actinic radiation that is located either inside or outside of the oral cavity. Preferably, the source of actinic radiation or light source is located outside of the patient's oral cavity, so that the light source does not inadvertently contact other appliances in the mouth or cause discomfort to the patient by contacting the patient's lips or cheeks. The optical fiber is disconnected from the appliance once the orthodontic adhesive has sufficiently hardened.

Figure 12:
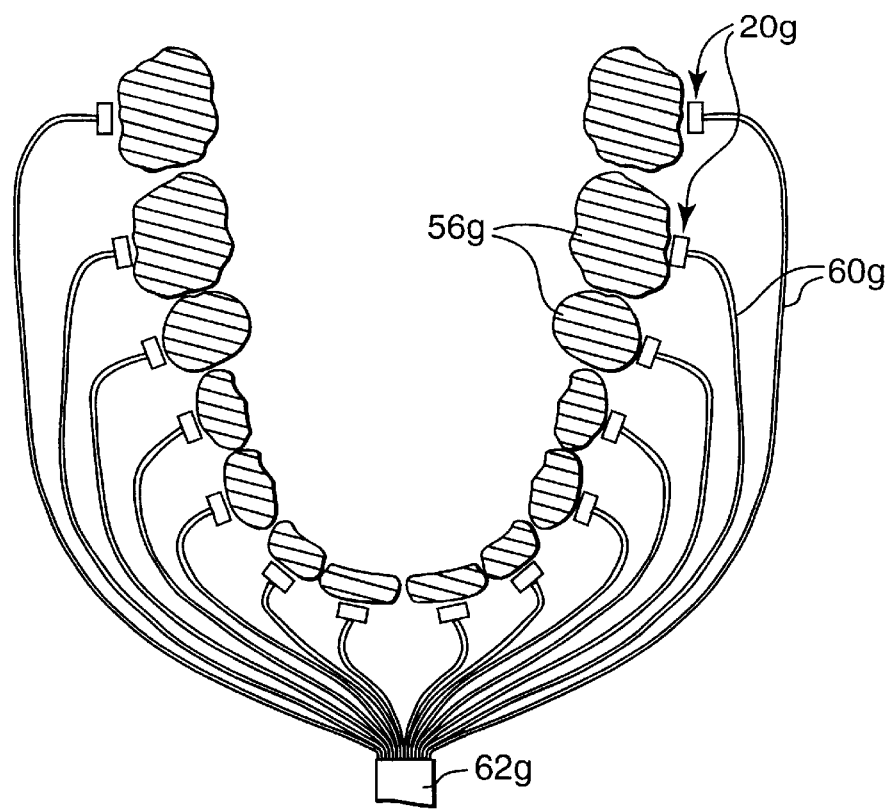
FIG. 12 is a plan view in schematic form of an exemplary dental arch, wherein a number of orthodontic appliance according to an additional embodiment of the invention are about to be bonded to corresponding teeth of the dental arch using a plurality of optical fibers.

An example of appliances connected to optical fibers as mentioned in the preceeding paragraph is illustrated in FIG. 12. In this example, a set of orthodontic appliances 20g is provided, one appliance 20g for each tooth 56g of a patient's dental arch. An optical fiber 60g leads from each appliance 20g to a manifold 62g. Preferably, but not necessarily, the manifold 62g is located outside of the patient's oral cavity.

Although not shown in FIG. 12, the manifold 62g is detachably connected to a source of actinic radiation. Preferably, the source of radiation has sufficient intensity, when activated, to cure all of the appliances 20g at once. Once the orthodontic adhesive has sufficiently hardened, the manifold 62g is disconnected from the source of actinic radiation and each of the optical fibers 60g is uncoupled from the associated appliance 20g.

Preferably, the optical fibers 60g can be disconnected from the associated appliances 20g by simply pulling on each fiber 60g until it fractures from the associated element of the appliance 20g. To this end, each optical fiber 60g has a rupture or tensile strength that is sufficiently low to allow the fiber 60g to be broken in this manner without pulling the associated appliance 20g off of the tooth. If desired, a line of weakness may be placed in each optical fiber 60g near the associated element of the appliance 20g to help ensure that the fiber 60g ruptures at a location close to the appliance 20g. Alternatively, a pair of fine-tipped wire cutters or other suitable hand instrument may be utilized to cut each fiber 60g at a desired location.

As another option, the fibers 60g may extend through the passageway of the appliance and along the base of the appliance 20g. As such, the portion of the fiber 60g that extends along the base of the appliance 20g functions in a manner similar to the optical fibers 54f that are described above in connection with the appliance 20f. Preferably, a number of fibers 60g extend through each passageway and along the base in radially outwardly fashion. The fibers 60g are fixed in place once a quantity of polymeric material is placed in the passageway and allowed to harden.

Figure 13:
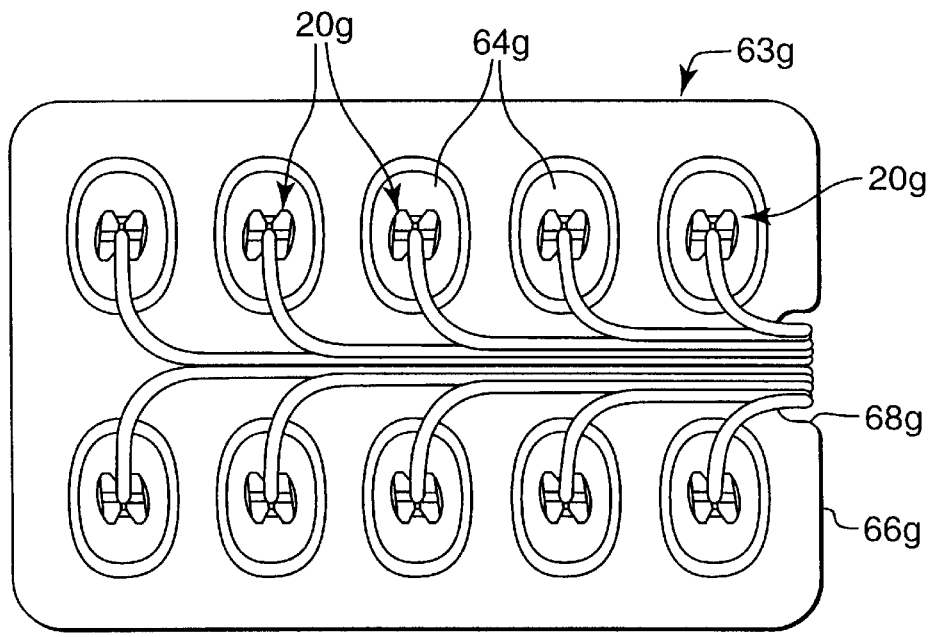
FIG. 13 is a plan view showing a preferred package for initially containing the orthodontic appliance and fibers that are illustrated in FIG. 12.

FIG. 13 is an illustration of an exemplary package 63g for containing the appliances 20g and the optical fibers 60g mentioned above (except that the package that is illustrated contains only ten appliances and not fourteen appliances). As shown, each of the appliances 20g is received in a well 64g of a substrate 66g. Optionally, each of the appliances 20g is precoated with a layer of light-curable orthodontic adhesive (such as the adhesive mentioned above). A cover (not shown) that is opaque to actinic radiation is then placed over the substrate 66g in such a manner that actinic radiation cannot reach the appliances 20g and the adhesive located within the well 64g.

The substrate 66g has a notch or opening 68g through which the fibers 60g initially extend. The opening 68g serves to retain the fibers 60g in a convenient array so that tangling of the fibers is avoided. A manifold (such as the manifold 62g) for the fibers 60g is not shown, but is located on the opposite side of the substrate 66g.

Figure 14:
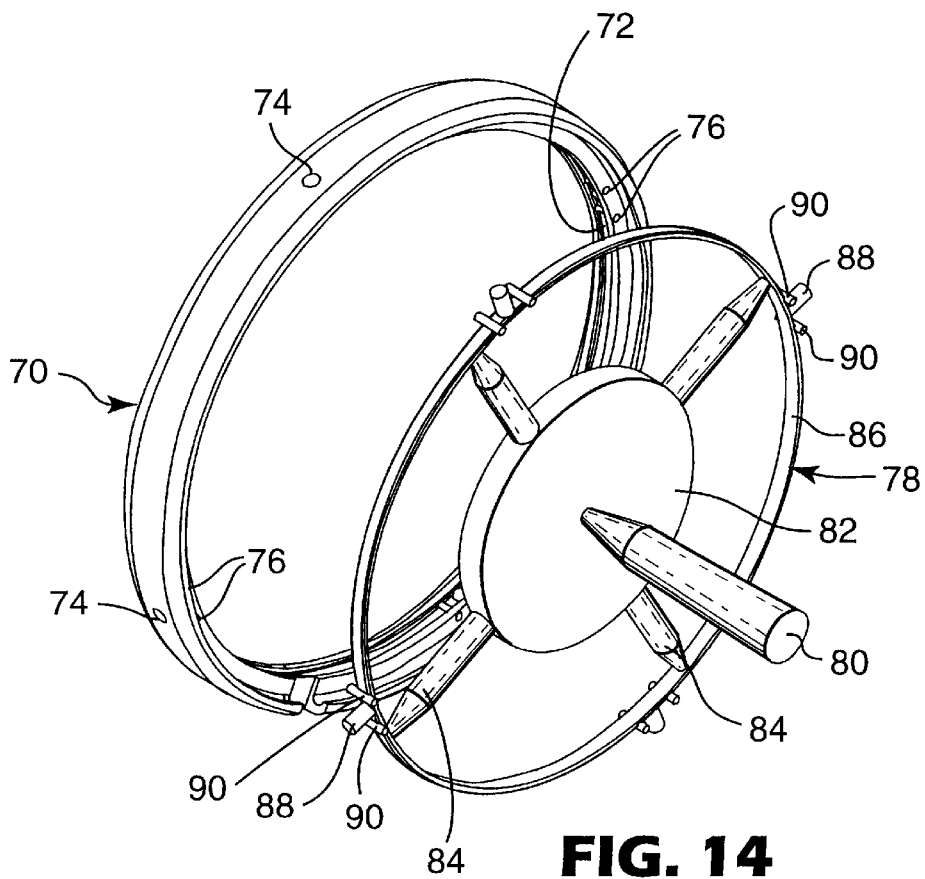
FIG. 14 is a perspective, exploded view illustrating one step of a method for making orthodontic appliances according to certain embodiments of the invention.

Another preferred method of manufacturing the orthodontic appliance according to the invention (such as the appliances 20–20g) is shown schematically in FIGS. 14–17. Referring initially to FIG. 14, a ring 70 is made of a metallic material such as one of the stainless steel materials described above. A channel 72 extends along the inner circumference of the ring 70 and extends in a plane that is perpendicular to a central axis of the ring 70. The channel 72 may be provided by any suitable process, such as a machining operation.

The ring 70 also includes a series of spaced apart passageways 74 that preferably extend radially inwardly toward the central axis of the ring 70. In the embodiment illustrated, only four passageways 74 are shown. However, it should be understood in this regard that the greater or smaller number of such passageways 74 may be provided if desired.

Optionally, the ring 70 also includes a series of holes 76 that extend through sides of the ring 70 in directions generally parallel to its central axis. For exemplary purposes, the ring 70 shown in FIG. 14 has been provided with eight holes 76, a pair of which straddle each passageway 74 in transverse relation. Each of the holes 76 extends from one side of the ring 70 to the other and also extends into the channel 72.

Once the ring 70 is provided with the channel 72, the passageways 74 and the holes 76, the ring 70 is placed in a mold cavity that is suitable for injection molding of polymeric material (such as polycarbonate). The polymeric material is then directed into the mold cavity where it enters the channel 72 as well as each passageway 74 and each hole 76. In FIG. 14, the component designated 78 represents an example of how the polymeric material might appear within the mold cavity, although the polymeric material is shown in exploded format separate from the ring 70 for purposes of illustration. The mold and the mold cavity are not shown in FIG. 14, although the shape of the mold cavity is the inverse of the shape of the component 78.

In more detail, the component 78 includes a central section 80 that is formed in an inlet passageway of the mold cavity. The central section 80 is connected to an intersecting section 82 that, in turn, leads to four radial sections 84. Each of the four radial sections 84 extends toward an outer annular section 86 that is formed in the channel 72 of the ring 70.

The annular section 86 is connected to four protrusions 88, each of which is received in a respective passageway 74 of the ring 70. Additionally, the annular section 86 is connected to eight crossbar sections 90, each of which is received in a respective hole 76 of the ring 70. As the polymeric material is forced into the mold cavity and into contact with the ring 70, the polymeric material conforms to the shape of the channel 72, the passageways 74 and the holes 76 so that a close, matching fit between the shape of the ring 70 and the hardened polymeric material is attained.

The shape of the mold cavity described in the preceding paragraphs may vary from the shape selected for exemplary purposes and illustrated in the drawings. For example, the mold cavity may have additional passageways so that additional radial sections similar to radial section 84 are presented. Also, the central section 80 and the intersection 82 may have shapes other than that shown in the drawings.

Once the polymeric material has hardened, the radial sections 84 are detached from the annular section 86 so that the radial sections 84, the intersection 82 and the central section 80 may be separated from the ring 70. Next, the ring 70 with the remaining portions of the hardened polymeric material are mounted in a milling machine for milling of orthodontic appliances. Examples of suitable techniques for ring milling of orthodontic appliances are described, for example, in U.S. Pat. Nos. 2,713,720 and 5,395,237, both of which are expressly incorporated by reference herein.

Figure 15:
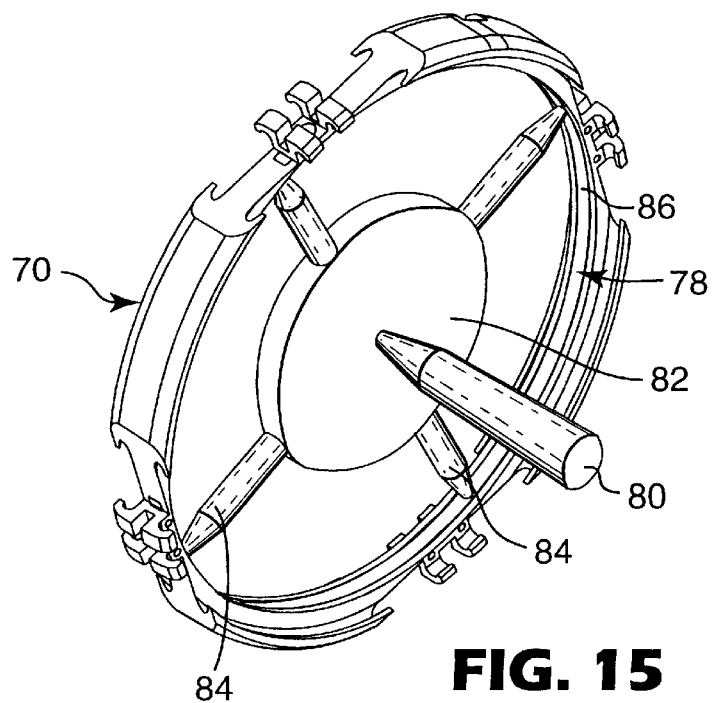
FIG. 15 is a perspective view showing a later step of the method described in connection with FIG. 14.

FIG. 15 is an illustration of the ring 70 as it appears during an intermediate stage of the ring milling technique. As depicted in FIG. 15, the tiewings, the archwire slot and portions of the body of the appliance have been milled to desired shapes. Next, the ring is milled in order to separate the individual appliances from each other and from remaining portions of the ring 70. Ring milling may be carried out using cutting tools such as a lathe, a milling machine or any other suitable tool.

Figure 16:
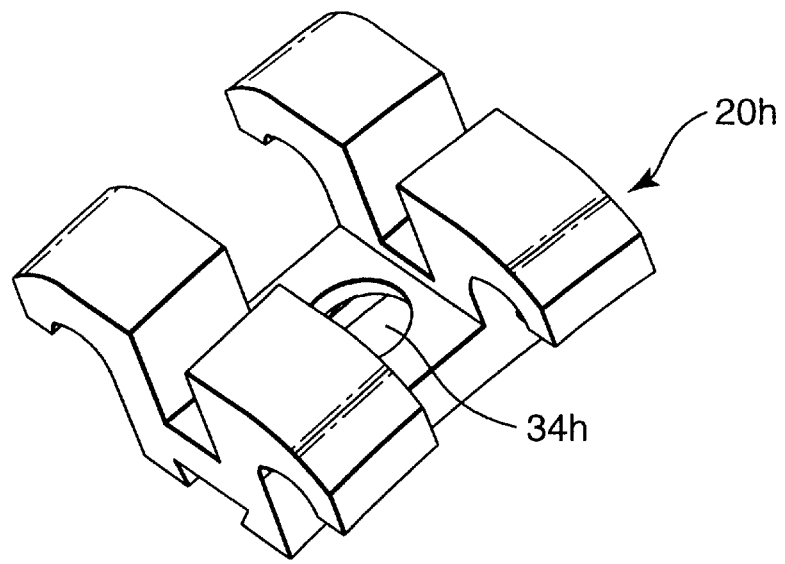
FIG. 16 is a perspective view of an orthodontic appliance made according to the methods described in connection with FIGS. 14 and 15.

FIG. 16 is an illustration of one of the four orthodontic appliances 20h that is made from the ring 70 shown in FIG. 15. The orthodontic appliance 20h is similar to the appliances 20–20g described above, in that it includes tiewings, an archwire slot and a body. In addition, the appliance 20h includes a light-transmissive element 34h made of the polymeric material described above that was received in the channel 72, the passageways 74 and the holes 76.

Figure 17:
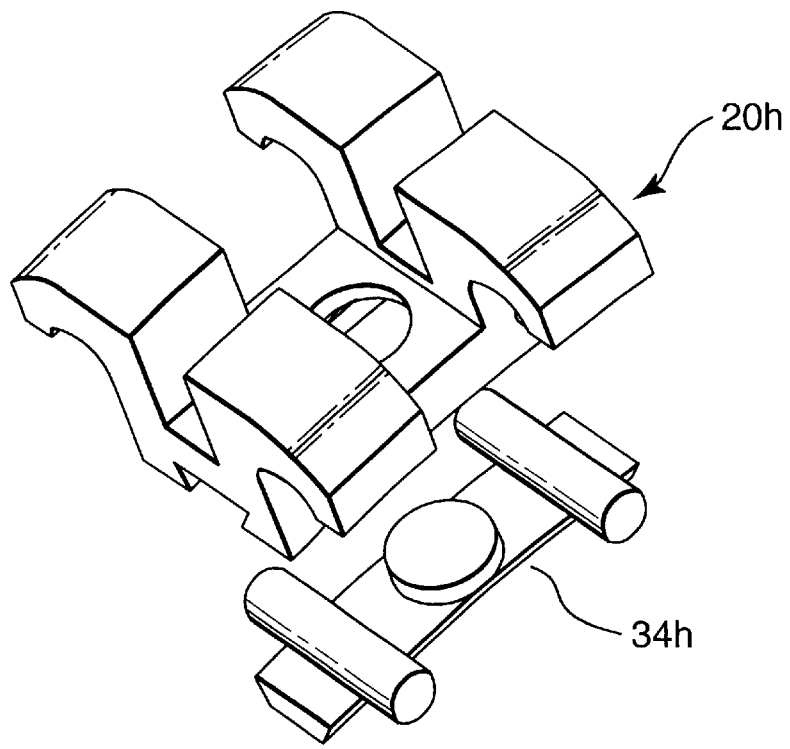
FIG. 17 is an exploded perspective view of the orthodontic appliance shown in FIG. 16.

FIG. 17 is an illustration of the appliance 20h shown in FIG. 16, except that the appliance 20h in FIG. 17 is illustrated in exploded form with the element 34h apart from remaining portions of the appliance 20h. As can be appreciated, the portions of the element 34h that comprised the crossbar sections 90 mentioned above provide a secure mechanical interlock with the remaining, metallic portion of the appliance 20h. As such, the element 34h is unlikely to become detached from remaining portions of the appliance 20h.

Although not shown in the drawings, the appliance 20h preferably includes a base such as the base 22 described in connection with the appliance 20. The base may be a mesh pad or a foil mesh pad that is brazed or welded to the underside of the body of the appliance 20h. Other aspects of the appliance 20h are similar to the aspects of the appliances described above. The element 34h serves to distribute actinic radiation to various regions of the adhesive underlying the appliance base when the appliance 20h is bonded to a tooth.

The appliances and the methods described above are representative of currently preferred embodiments of the invention. Those skilled in the art, however, will recognize that a number of modifications and additions may be made to the illustrated appliances and described methods without departing from the essence of the invention. Moreover, the invention is useful with other types of orthodontic appliances as well, such as buccal tubes, lingual buttons, lingual cleats, surgical buttons and surgical cleats. As such, the invention should not be deemed limited to the specific embodiments that are described in detail above, but instead only by a fair scope of the claims that follow along with their equivalents.

What is claimed is:

1. An orthodontic appliance for attachment to a tooth comprising:
    a base having an outer surface;
    a body extending from the base in a direction away from the outer surface;
    a slot next to the body for receiving an archwire;
    a passageway extending through the base; and
    an element extending in the passageway, the element being made of a material that transmits actinic radiation.

2. An orthodontic appliance according to claim 1 wherein the element closes the passageway.

3. An orthodontic appliance according to claim 1 wherein the element is fixed in the passageway.

4. An orthodontic appliance according to claim 1 wherein the material releases fluoride.

5. An orthodontic appliance according to claim 1 wherein the passageway includes at least one tapered portion that increases in cross-sectional area as the outer surface is approached.

6. An orthodontic appliance according to claim 1 wherein the passageway includes at least one shoulder.

7. An orthodontic appliance according to claim 1 wherein the passageway also extends through the body.

8. An orthodontic appliance according to claim 7 wherein the passageway extends through a central portion of the body.

9. An orthodontic appliance according to claim 1 wherein the appliance is a bracket, buccal tube, cleat or button.

10. An orthodontic appliance according to claim 1 and including at least one additional passageway extending through the base and an element received in each additional passageway, each element being made of a material that transmits actinic radiation.

11. An orthodontic appliance according to claim 1 wherein the element has a color that contrasts with at least one of the body and the base.

12. An orthodontic appliance according to claim 11 wherein the color represents a code that identifies one or more teeth.

13. An orthodontic appliance according to claim 1 and including one or more grooves for facilitating alignment of the appliance with the tooth, and wherein each groove receives a material that is the same as the material of the element.

14. An orthodontic appliance according to claim 1 and including at least one optical fiber extending across at least a portion of the outer surface of the base.

15. An orthodontic appliance according to claim 14 wherein each optical fiber has a first end that is located near the passageway.

16. An orthodontic appliance according to claim 14 wherein each optical fiber has a first end that is embedded in the element.

17. An orthodontic appliance according to claim 16 wherein the base has a periphery, and wherein each optical fiber extends toward the periphery of the base when the appliance is attached to a tooth.

18. An orthodontic appliance according to claim 17 wherein the appliance includes a number of optical fibers that extend radially toward the periphery of the base when the appliance is attached to a tooth.

19. An orthodontic appliance according to claim 1 and including a quantity of light-curable orthodontic adhesive extending across the base and the element.

20. An orthodontic appliance according to claim 1 wherein the appliance also includes a hole extending at an angle relative to the direction of extension of the passageway and wherein a portion of the element extends in each hole.

21. An orthodontic appliance according to claim 20 wherein at least one hole extends in a direction perpendicular to the direction of extension of the passageway.

22. An orthodontic appliance according to claim 1 wherein the element includes at least one protrusion next to the base.

23. A method of bonding an orthodontic appliance to a tooth comprising:
   providing an orthodontic appliance having a passageway that extends toward a base of the appliance and an element extending in the passageway;
   placing a quantity of light-curable adhesive on the base of the appliance;
   placing the appliance on a tooth; and
   directing actinic radiation through the passageway and the element in order to facilitate curing of the adhesive.

24. A method of bonding an orthodontic appliance to a tooth according to claim 23 wherein at least a portion of the element is fixed in the passageway, and wherein the act of placing a quantity of light-curable adhesive on the base of the appliance includes the act of placing a portion of the adhesive across at least part of the element.

25. A method of bonding an orthodontic appliance to a tooth according to claim 23 and including the act of initially placing the appliance in a package after the act of placing a quantity of photocurable adhesive on the base of the appliance and prior to the act of placing the appliance on the tooth.

26. A method of bonding an orthodontic appliance to a tooth according to claim 23 wherein the act of directing actinic radiation to the passageway and through the element includes the act of directing at least a portion of the actinic radiation through one or more optical fibers.

27. A method of bonding an orthodontic appliance to a tooth according to claim 26 wherein the act of directing at least a portion of actinic radiation through one or more optical fibers includes the act of directing at least a portion of the actinic radiation through one or more optical fibers that extend toward a periphery of the base.

28. A method of bonding an orthodontic appliance to a tooth according to claim 26 wherein the act of directing at least a portion of the actinic radiation through one or more optical fibers includes the act of directing at least a portion of the actinic radiation in a radial direction away from the passageway.

29. An orthodontic appliance for attachment to a tooth comprising:
   a base having an outer surface;
   at least one passageway extending through the base;
   a body extending from the base in a direction away from the outer surface;
   an orthodontic adhesive extending across at least a portion of the outer surface; and
   at least one optical fiber received in the orthodontic adhesive and extending along the base, wherein the at least one optical fiber extends toward the at least one passageway.

30. An orthodontic appliance according to claim 29 wherein a number of optical fibers are provided, and wherein each optical fiber extends radially outwardly from the passageway.

31. An orthodontic appliance according to claim 29 wherein an element extends in the passageway, wherein the element is made of a material that transmits actinic radiation, and wherein the element is connected to each optical fiber.

32. An orthodontic appliance according to claim 29 and including a package surrounding the appliance, wherein the package substantially prevents the transmission of actinic radiation to the adhesive.

33. A method of bonding an orthodontic appliance to a tooth comprising:
   providing an orthodontic appliance having a base with an outer surface;
   placing a quantity of light-curable adhesive on the outer surface;
   placing at least one optical fiber in the adhesive;
   positioning the appliance on the tooth; and
   directing a source of actinic radiation toward the at least one optical fiber in order to enhance distribution of the actinic radiation in the adhesive, wherein the act of placing at least one optical fiber in the adhesive includes the act of placing at least one optical fiber in a direction extending along the outer surface of the base in a radial direction from a central region of the outer surface.

34. A method of bonding an orthodontic appliance to a tooth according to claim 23 wherein a number of optical fibers are provided and placed in the adhesive, and wherein each optical fiber extends radially outwardly from the central region of the outer surface.

35. A method of bonding an orthodontic appliance to a tooth according to claim 33 and including the act of initially placing the appliance and the adhesive in a package that hinders passage of actinic radiation prior to the act of positioning the appliance on the tooth.

36. A method of bonding an orthodontic appliance to a tooth according to claim 33 wherein the at least one optical fiber in the adhesive extends toward a periphery of the base.

37. A method of bonding an orthodontic appliance to a tooth comprising:

providing an orthodontic appliance having a base with an outer surface;

placing a quantity of light-curable adhesive on the outer surface;

placing at least one optical fiber in the adhesive;

positioning the appliance on the tooth; and directing a source of actinic radiation toward the at least one optical fiber in order to enhance distribution of the actinic radiation in the adhesive, wherein the act of directing a source of actinic radiation toward the at least one optical fiber includes the act of directing a source of actinic radiation through a passageway of the appliance.

38. A method of bonding an orthodontic appliance to a tooth according to claim 37 wherein the act of placing at least one optical fiber in the adhesive includes the act of placing at least one optical fiber in a direction extending along the outer surface of the base.

39. A method of bonding an orthodontic appliance to a tooth according to claim 38 wherein the at least one optical fiber extends in a radial direction from a central region of the outer surface.

40. A method of bonding an orthodontic appliance to a tooth according to claim 37 wherein the act of directing a source of actinic radiation toward the at least one optical fiber includes the act of directing actinic radiation along the fiber in a radial direction away from a central region of the outer surface of the base.

* * * * *

UNITED STATES PATENT AND TRADEMARK OFFICE
CERTIFICATE OF CORRECTION

PATENT NO.    : 6,482,002 B2
DATED         : November 19, 2002
INVENTOR(S)   : Jordan, Russell A.

It is certified that error appears in the above-identified patent and that said Letters Patent is hereby corrected as shown below:

<u>Title page,</u>
Item [56], FOREIGN PATENT DOCUMENTS, delete "9" and insert in place thereof -- 5 --.

<u>Column 19,</u>
Line 2, delete "23" and insert in place thereof -- 33 --.

Signed and Sealed this

Twenty-third Day of September, 2003

JAMES E. ROGAN
*Director of the United States Patent and Trademark Office*